(12) United States Patent
Ryan

(10) Patent No.: US 6,358,226 B1
(45) Date of Patent: Mar. 19, 2002

(54) LACTATION APPARATUS

(76) Inventor: Audrey M. Ryan, P.O. Box 516, Nellys Ford, VA (US) 22958

( * ) Notice: Subject to any disclaimer, the term of this patent is extended or adjusted under 35 U.S.C. 154(b) by 57 days.

(21) Appl. No.: 09/599,804

(22) Filed: Jun. 21, 2000

(51) Int. Cl.$^7$ .............................. A61M 1/06; A61F 7/12
(52) U.S. Cl. ......................................... 604/74; 604/113
(58) Field of Search ............................ 604/73–76, 113, 604/114; 607/96, 104, 108; 119/14.01

(56) References Cited

U.S. PATENT DOCUMENTS

| | | |
|---|---|---|
| 2,298,361 A | 10/1942 | Freund |
| 4,391,221 A * | 7/1983 | Hoefelmayr et al. ..... 119/14.08 |
| 4,584,992 A * | 4/1986 | Liu ........................... 128/24.1 |
| 4,740,196 A | 4/1988 | Powell |
| 5,050,595 A | 9/1991 | Krafft |
| D324,915 S | 3/1992 | Wastchak |
| 5,304,215 A | 4/1994 | MacWhinnie et al. |
| 5,441,534 A | 8/1995 | MacWhinnie et al. |
| 5,476,490 A | 12/1995 | Silver |
| 5,514,166 A | 5/1996 | Silver et al. |
| 5,571,084 A | 11/1996 | Palmer |
| 5,575,768 A | 11/1996 | Lockridge et al. |
| 5,679,052 A | 10/1997 | Rucki |
| 5,776,177 A | 7/1998 | MacWhinnie et al. |
| 5,897,580 A | 4/1999 | Silver |

* cited by examiner

Primary Examiner—Sharon Kennedy
(74) Attorney, Agent, or Firm—John P. Sinnott; Langdale, Vallotton, Linahan & Wetherington, L.L.P.

(57) ABSTRACT

A breast pump for continuously applying warmth at a temperature of not more than about 105 degrees Fahrenheit to a mammary gland both before and during milk withdrawal is described. The apparatus enables the mammary gland tissue to be raised to a temperature that makes milk withdrawal more comfortable, whereupon suction is applied to the gland, as the temperature is maintained in order to commence the withdrawal process and permit the milk so extracted to be administered artificially to a suckling infant.

19 Claims, 2 Drawing Sheets

LACTATION APPARATUS

BACKGROUND OF THE INVENTION

1. Field of the Invention

This invention relates to improvements in methods and apparatus for withdrawing milk from lactating mammary glands and, more particularly, to methods and apparatus for selectively and continuously warming to a predetermined temperature the mammary gland tissue while suction is applied to extract milk therefrom, and the like.

2. Background Prior Art

Pressures, both economic and social, place the mother of a newborn infant in a very difficult situation. For example, the overwhelming body of medical opinion is of the view that milk, drawn from the breasts of a properly nourished mother, is the best possible food for her newborn child. The conflicting need for the mother to return to work as swiftly as possible and a reluctance to nurse an infant in public places, however, are major impediments to the preferred natural feeding regimen.

Though the years, breast pumps have been developed to enable the lactating mother to withdraw milk from her breasts and store it to feed the infant at a later time when suckling otherwise might be awkward, inconvenient or impossible.

There are, of course, further situations in which breast pumps are helpful. Illustratively, some infants do not suckle very well and require the assistance of an artificial nipple and bottle combination in order to draw adequate nourishment. In this circumstance, withdrawing the mother's milk through a breast pump and transferring that milk to a nursing bottle for administration to the child may offer an acceptable method for feeding mother's milk to the child.

Breast pumps, moreover, are not limited in their application to human beings. Among the industrialized nations, milking machines are, perhaps, the most common way in which milk is extracted from cattle for commercial purposes. Although these machines are a more efficient way to produce milk, studies have shown that manual extraction of milk by milk maids actually results in appreciably greater milk production from the animals. Toward this end of increased milk production, various approaches have been tried with occasional success, e.g., playing soothing music in the barn during milking.

None of these breast pump developments have been entirely satisfactory. For instance, there is a continuing need for an improved apparatus that is capable of increasing animal milk production. Human nursing needs, moreover, appear to be considerably more complicated. In this respect, the suction apparatus for some breast pumps are applied only to the nipple and offer no support to the balance of the breast. A disadvantage to this device is the requirement for the nursing mother to use both hands in order to extract the milk—one hand to support the breast and the other hand to manipulate the pump. Further in this regard, if the nursing breast is not properly supported the subsequent milk withdrawal can be uncomfortable or, possibly, even painful.

As a general matter, it has been found that milk extraction is eased and made less uncomfortable if the mammary gland tissue is warmed immediately before and during the course of the extraction procedure.

Earlier breast pumps relied on pre-heated compresses that lost their heat as the milk was withdrawn. These devices thus were quite inefficient because they were incapable of maintaining a predetermined temperature during the extraction process.

Consequently, there is a need for an improved breast pump that can reduce the discomfort and inconvenience that heretofore has characterized application of these devices.

BRIEF DESCRIPTION OF THE INVENTION

These and other limitations that have characterized the prior art are overcome, to a large extent, through the practice of the invention. Illustratively, a breast cup is provided to support not less than one half of the exposed surface of a lactating breast. The cup has a soft innermost portion that bears directly against the surface of the mammary gland. This innermost portion encapsulates a heat transmitting gel that conforms to the shape of he individual breast.

A middle portion of the cup forms a void space that generally matches the area of the innermost portion. This void space within the middle portion accommodates a warmed, working fluid that transfers its warmth through the gel to the lactating mammary gland in order to promote and make more comfortable the extraction of milk from the breast.

A firm, outermost portion of the cup not only houses the middle and innermost cup portions but also provides physical support for the breast and the suction and heating connections. In this respect, a heating tube passes through the outermost portion in order to establish working fluid communication with the void space within the middle cup portion.

A suction device protrudes through the cup structure at a place that approximates the location of the nipple on the mammary gland. The suction device has an inner annulus that approximates the size and shape of a typical nipple. The suction device also has a centrally disposed conduit that establishes fluid communication between the nipple and a "T" coupling inlet. One of the two remaining passageways in the "T", coupling is a discharge outlet that communicates with a reservoir for collecting the milk sucked from the breast. The other "T" coupling passageway is a vacuum port that communicates with the suction pump to apply the necessary degree of vacuum to the nipple for milk withdrawal. A suction tube couples the conduit in the suction device to a selectively energizable suction pump through the other "T", coupling passageway.

The heating tube extends from the outermost portion of the cup to a thermostatically controlled heating element that maintains the temperature of the innermost portion of the cup that is applied to the breast surface at a predetermined and preferable temperature in the range of 105° F. to 110° F. The heating element also is activatable separately from the suction pump to enable the breast tissue to be warmed selectively before, during and after milk withdrawal, according to the needs and comfort characteristics of the lactating individual.

These and other features of the invention will become apparent through a study of the following detailed description of an illustrative embodiment of the invention. The scope of the invention, however, is limited only through the claims appended hereto.

DETAILED DESCRIPTION OF THE INVENTION

Figure 1:
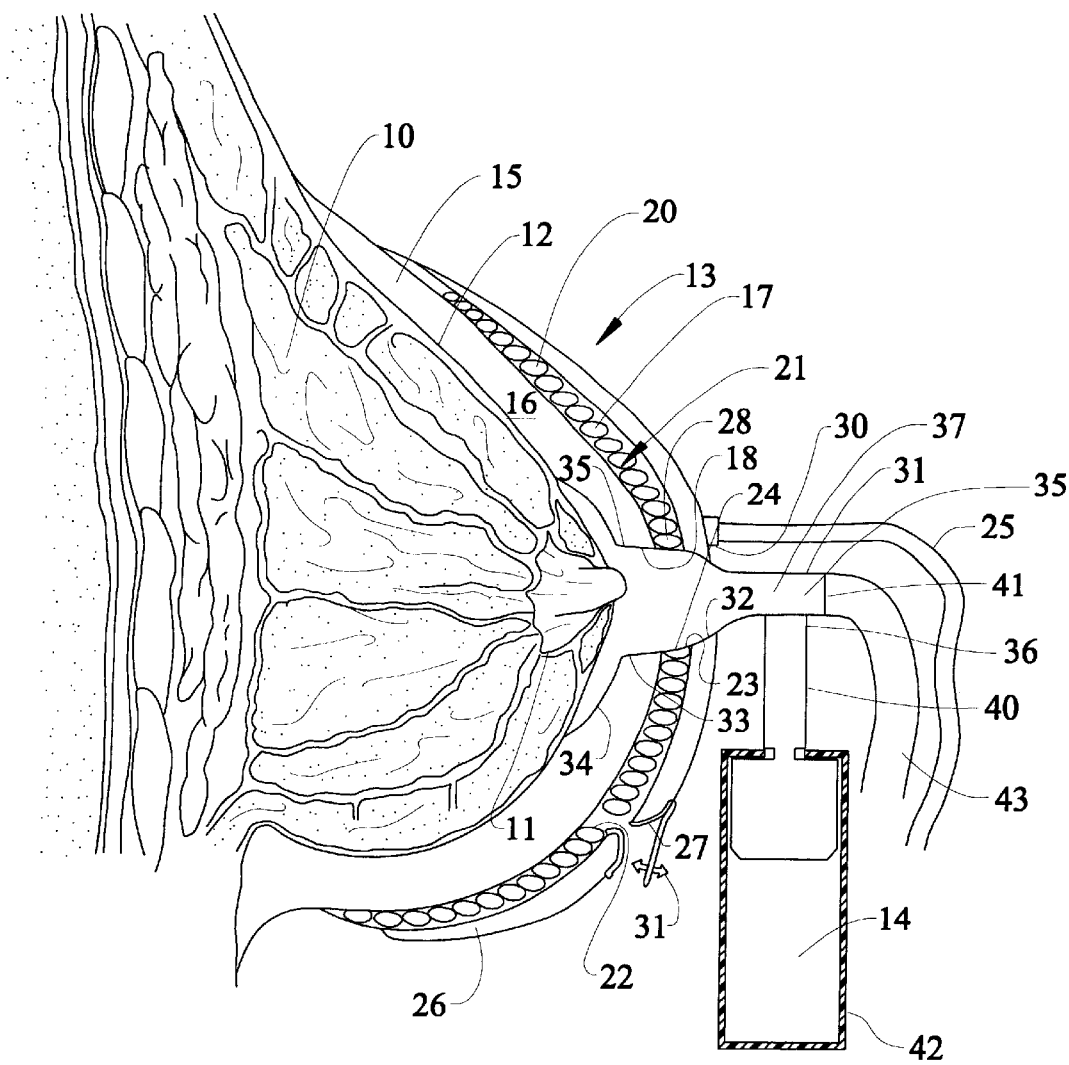
FIG. 1 is a side elevation in full section of a portion of an illustrative embodiment of the invention.

For a more complete appreciation of the invention, attention is invited to FIG. 1 which shows a lactating mammary gland 10 that terminates in a nipple 11. Outer surface 12 of the gland 10 is enclosed in a cup 13. As illustrated, the cup 13 covers the entire outer surface 12 of the gland 10. In accordance with a salient feature of the invention, the cup 13 should cover not less than one-half of the outer surface 12 of the gland 10 in order to provide physical support to the breast and thus to enhance the comfort of the person from whom milk 14 is being withdrawn.

The cup 13 has a soft and pliable innermost portion 15 that is filled with a heat conducting gel 16 in order to conform to the shape of the gland 10 and warm the gland 10 as described subsequently in more detail. The heat conducting gel 16 can be any suitable material, of which a silicone gel is illustrative. The innermost portion 15 also has a centrally disposed bore 18 in general alignment with the nipple 11.

A middle portion 17 of the cup 13 is formed of rubber, or the like. The middle portion 17 is joined to the innermost portion 15 and overlays a somewhat smaller area of the outer surface 12 of the gland 10 than the innermost portion 15. As shown, the middle portion 17 not only lends structural support to the pliable innermost portion 15, but also forms a void space 20. The illustrative embodiment of the invention in FIG. 1 shows the void space 20 as an array of interconnecting passageways 21 which terminate in a passageway 22 that selectively communicates with the ambient atmosphere and an inlet passageway 24 that is coupled to a warm working fluid or air supply tube 25. A baffle 28 in the interconnecting passageways 21 is placed in the middle portion 17, generally aligned with the warm air supply coupling 30 on the outermost portion 26 to better distribute inflowing warm air through the interconnecting passageways 21 and thus to avoid the development of a "hot spot" within the structure of the cup 13. A further bore 23 is formed in the middle portion 17, generally aligned with the nipple 11 and the bore 18 in the innermost portion 15.

Firm, outermost portion 26 of the cup 13 is formed of a fairly stiff (but not hard) molded plastic. As illustrated, the outermost portion 26 is joined to the surface of the middle portion 17 and has a passageway 27 in alignment with the warm air discharge passageway 22 in the middle portion 17. Another passageway, not shown in the drawing, is aligned with the warm air inlet passageway 24 in the middle portion 17. A coupling 30 on the exposed external surface of the outermost portion 26 joins the warm air supply tube 25 to the cup 13 in order to establish fluid communication between the warm air supply tube 25 and the passageways 21 within the middle portion 17.

An elastic warm air pressure release valve 31 controls the flow of warm air from the communicating passageways 22 and 27 to the atmosphere to maintain a throughput of warm air within the passageways, stabilize the temperature of the gel 16 and prevent the middle portion 17 from inflating.

The size of the outermost portion 26 of the cup 13 is generally the same as the size of the middle portion 17, the outermost portion 26 being generally coextensive with the middle portion 17 to which it is joined. A bore 32 also is formed in the outermost portion 26 that is axially aligned with the bores 23 and 18 in the middle and innermost portions 17 and 15, respectively, of the cup 13.

The axially aligned bores 18, 23 and 32 in the cup 13 accommodate a suction device 33. Typically, the suction device 33 has an annulus 34 that generally covers the surface of the nipple 11. Central portion 35 of the suction device 33 is hollow and is seated in the bores 18, 23 and 32, to protrude from the cup 13 and establish fluid communication with a "T" coupling 36.

As illustrated, the "T" coupling 36 has an inlet 37 that communicates with a milk discharge outlet 40 and a vacuum port 41. Further in this regard, the milk discharge outlet 40 is detachably connected to breast milk receptacle 42. The receptacle 42 enables milk, sucked from the nipple 11 to accumulate in the receptacle 42 while permitting a suitable vacuum to be applied through the port 41 in the manner described subsequently in more complete detail.

Figure 4:
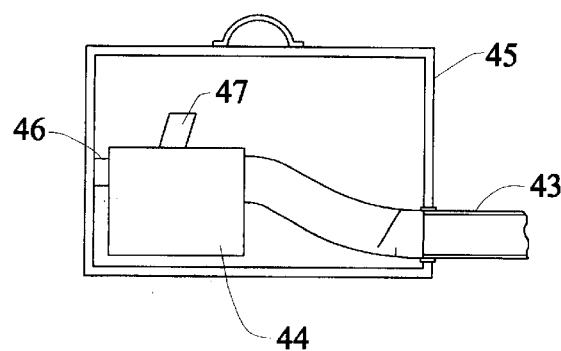
FIG. 4 is a side elevation of a typical suction apparatus embodying principles of the invention.

A vacuum tube 43 establishes suction between the central portion 35 of the suction device 33 and, as illustrated in FIG. 4, a suction pump 44. The suction pump 44 is conveniently mounted in a carrying case 45 that has an air discharge port 46 to enable air, drawn through the suction tube 43 to dissipate in the atmosphere. A suction control 47 is also provided for the suction pump 44. The control 47 permits the lactating woman to adjust the vacuum applied to the nipple 11 (FIG. 1) in accordance with individual needs, e.g., a gentle pulsating vacuum, steady application of vacuum at a comfortable level, and the like.

Figure 3:
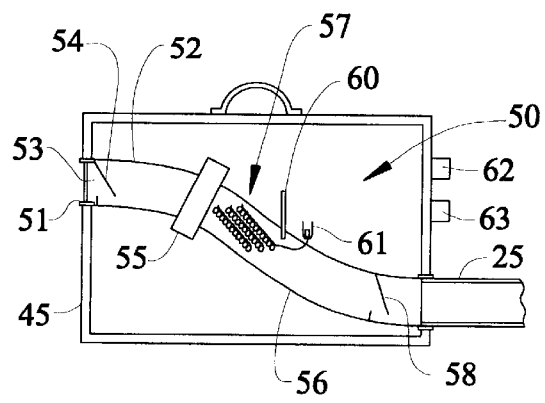
FIG. 3 is a schematic side elevation of a typical heating apparatus in accordance with principles of the invention.

Within the carrying case 45, as shown in FIG. 3, air warming apparatus 50 also is provided. As illustrated, the carrying case 45 has an air inlet port 51 connected to an air inlet conduit 52 that provides a pathway from the ambient atmosphere, through an air filter 53 and a one-way air check valve 54 to an air pump 55. The air pump 55 draws air from the atmosphere and discharges the air at a suitable pressure to a pressurized air tube 56 with a one-way check valve 58. Heating elements 57 mounted within the pressurized air tube 56 warm the air that is discharged from the pump 55 to a predetermined temperature that is registered by a heat sensor 60. The heat sensor 60, in turn, automatically activates and deactivates a switch 61 in order to prevent the temperature of the heated and pressurized air from exceeding a predetermined maximum, which should be about 116° F. This selected maximum temperature for the air as it passes through the heating elements 57 should deliver air to the baffles 28 (FIG. 1) in the cup 13 at a temperature of not more than 105° F. to 110° F. This upper limit temperature range, 105° F. to 110° F., has been identified as the maximum temperature that can be applied to a typical breast and promote comfortable lactation without risk of injury to the mammary gland 10.

Further in this respect, personal preferences, physiological differences and the like necessarily raise a need for flexibility in the way in which the glandular tissue is warmed in order to satisfy a range of individual requirements. The time required not only to warm the breast tissue to a suitable temperature but also to continue to warm the tissue to that temperature before suction is applied to the nipple typically will vary from person-to-person.

There also is a need, in accordance with the invention, to maintain a predetermined breast tissue temperature during the entire extraction process to assist in the complete and comfortable withdrawal of all of the milk from the breast.

Accordingly, the air warming apparatus is supplied with a separate power switch 62 (FIG. 3) to activate the air pump 55, the heating elements 57, the heat sensor 60 and the selectively activatable temperature limits switch 61. A manual temperature control 63, however, is provided to permit the lactating woman to adjust the air temperature to some individually more comfortable level that is below the maximum temperature set by the heat sensor 60 and its associated switch 61.

Figure 2:
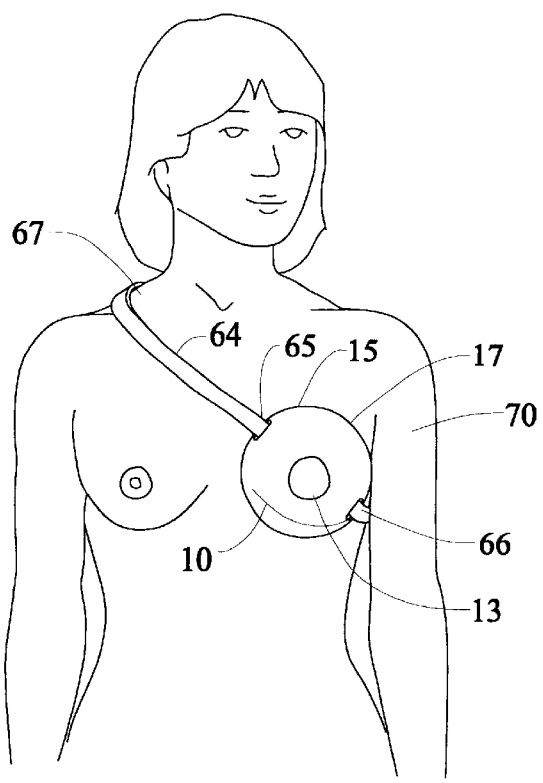
FIG. 2 is a front elevation of the portion of the invention shown in FIG. 1.

An additional feature is illustrated in FIG. 2. As shown in FIG. 2, an adjustable strap 64 is attached by its ends 65, 66 to diametrically opposite sides of the innermost portion 15 of the cup 13 that protrudes beyond the perimeter of the middle portion 17. The strap 64 is slung over shoulder 67 of the lactating woman on the side that is opposite to the breast from which the milk is being withdrawn. The strap 64 is looped under the arm 70 in order to press the cup 13 against the lactating breast in a manner that holds the cup 13 in proper position with respect to that breast while freeing both of the woman's hands.

In operation, the cup 13 is applied to the mammary gland 10 and the strap 64 is adjusted to hold the cup 13 in place over the breast. It may be the preference of the lactating woman to warm the breast tissue to a suitable temperature before suction is applied to the nipple 11 (FIG. 1). Accordingly, and as illustrated in FIG. 3, the power switch 62 is manipulated to energize the air pump 55; warm the heating elements 57; and activate the heat sensor 60 with its associated automatic temperature limit switch 61. The manual temperature control 63 is then operated to lower the heated air temperature to a level that the individual user finds most comfortable for withdrawal.

After a suitable period of time, the time depending on the physiology of the individual woman, the lactating breast tissue has warmed to a level that will promote milk flow and the suction control 47 (FIG. 4) is operated to produce suction in a manner and with a pressure that is individually comfortable for the lactating woman. The suction pump 44 draws air through the vacuum tube 43 in order to apply suction to the nipple 11 (FIG. 1) through a path that includes the suction device 33; the inlet 37 to the "T" coupling 36; the vacuum port 41; and the check valve 58 (FIG. 3). The breast milk 14 that is drawn from the nipple 11, drains, under gravity, into the breast milk receptacle 42.

Meanwhile, warm air continues to flow through the air tube 56 (FIG. 4) from the carrying case 45 to warm the mammary gland 10 (FIG. 1) through a path that includes the warm air supply tube 25, the inlet passageway 24, the baffle 28, the void space 20, the passageways 22, 27 and the pressure relief valve 31. The heat, so supplied to the void space 20 and surface of the middle portion 17, is transferred to the gel 16 in the innermost portion 15. The nature of the gel 16 is such that it distributes this warmth in a generally uniform manner over the entire surface of the breast with which the innermost portion 15 is in contact. This application of warmth to the breast, for the purpose of reducing the discomfort that hitherto had been associated with pumped milk withdrawal, can be maintained at the predetermined temperature (or temperatures) as long as desired.

To deactivate the apparatus, it is only necessary to turn off the suction control switch 47 (FIG. 4) and the power switch 62. The now de-energized manual temperature control 63 (FIG. 3) need not be changed, but can be left at the preferred setting for later use. The cup 13 (FIG. 2) and strap 64 can be removed from the shoulder 67 and the mammary gland 10, the breast milk receptacle 42 also can be removed from the structure and its contents poured into a nursing bottle for subsequent infant feeding.

There are, moreover, a number of modifications that can be made to the specific embodiment of the invention described above while remaining, nevertheless, within the scope of the invention. Illustratively, some working fluid for transferring warmth to the mammary gland other than air can be used, e.g., water. This working fluid also can be re-circulated to provide further thermal efficiency. Combining the suction and air pumps into one unit is also possible to effect further savings.

What is claimed is:

1. An apparatus for withdrawing milk from a mammary gland comprising:
   a cup for supporting the gland,
      said cup having a void space formed therewithin and a bore penetrating said cup,
   a suction device received in said bore,
      said suction device establishing fluid communication with the gland,
   a suction pump in fluid communication with said suction device for selective application of suction to the gland,
   a working fluid,
   a pump for applying said working fluid to said void space,
   at least one heating element for selectively warming said working fluid, and
   a temperature control for adjusting said heating element to warm said working fluid to a predetermined temperature, whereby said warmed working fluid in said void space warms the gland and promotes the withdrawal of milk from the mammary gland through said suction device.

2. An apparatus according to claim 1 wherein said cup supports at least one-half of the surface of the gland.

3. An apparatus according to claim 1 wherein said cup further comprises an innermost portion for bearing against and generally conforming to the shape of the gland.

4. An apparatus according to claim 3 wherein said innermost cup portion encapsulates a gel for conforming to the shape of the gland and for transferring warmth from said working fluid to the gland.

5. An apparatus according to claim 1 wherein said cup further comprises a middle portion that bears against said innermost cup portion, said innermost portion forming said void space.

6. An apparatus according to claim 5 wherein said innermost portion has a plurality of passageways for forming said void space.

7. An apparatus according to claim 5 further comprising a pressure release valve in fluid communication with said void space.

8. An apparatus according to claim 1 wherein said cup further comprises an outermost portion to support the gland as milk is being withdrawn therefrom.

9. An apparatus according to claim 1 further comprising a strap for securing at least part of said apparatus to the gland.

10. An apparatus according to claim 1 further comprising a coupling in fluid communication with said suction device, said coupling having an inlet for enabling the milk to flow into said coupling, a milk discharge outlet on said coupling to drain the milk from the coupling and a vacuum port on said coupling to apply suction from said suction device to the gland.

11. An apparatus according to claim 10 further comprising a selectively removable milk receptacle for collecting milk from said milk discharge outlet.

12. An apparatus according to claim 11 further comprising a vacuum tube for establishing fluid communication between said vacuum port and said suction pump.

13. An apparatus according to claim 1 further comprising a suction control for applying a predetermined suction to the gland in order to withdraw the milk.

14. An apparatus according to claim 1 further comprising a power switch for activating and deactivating said heating element independently of said suction pump.

15. An apparatus according to claim 1 further comprising a heat switch for automatically de-energizing said heating element in response to a predetermined temperature for said working fluid.

16. An apparatus according to claim 15 further comprising a temperature sensor in thermal communication with said working fluid for controlling said heat switch in response to said working fluid temperature.

17. An apparatus according to claim 16 wherein said working fluid pump re-circulates said working fluid through said heating element and said void space.

18. An apparatus according to claim 16 further comprising a supply tube for coupling said working fluid pump to said void space.

19. An apparatus according to claim 18 wherein said working fluid comprises air.

* * * * *